(12) United States Patent
Peng

(10) Patent No.: US 6,629,444 B2
(45) Date of Patent: Oct. 7, 2003

(54) METHOD AND APPARATUS FOR DIAGNOSING GAS SENSORS

(75) Inventor: Wenfeng Peng, Mississauga (CA)

(73) Assignee: Industrial Scientific Corporation, Oakdale, PA (US)

( * ) Notice: Subject to any disclaimer, the term of this patent is extended or adjusted under 35 U.S.C. 154(b) by 244 days.

(21) Appl. No.: 09/923,964

(22) Filed: Aug. 8, 2001

(65) Prior Publication Data

US 2003/0033848 A1 Feb. 20, 2003

(51) Int. Cl.[7] .............................................. F16K 19/00
(52) U.S. Cl. ....................................................... 73/1.06
(58) Field of Search ................................. 73/1.02, 1.03, 73/1.06, 1.07; 204/401

(56) References Cited

U.S. PATENT DOCUMENTS

| | | | |
|---|---|---|---|
| 4,590,789 A | * | 5/1986 | Kunze .......................... 73/1.06 |
| 4,645,572 A | * | 2/1987 | Nishizawa et al. |
| 5,281,314 A | * | 1/1994 | Yagi et al. |
| 5,614,655 A | * | 3/1997 | Horn ............................ 73/1.06 |
| 5,939,615 A | * | 8/1999 | Kato et al. |

* cited by examiner

*Primary Examiner*—Robert Raevis
(74) *Attorney, Agent, or Firm*—Dennison, Schultz & Dougherty

(57) ABSTRACT

A method and apparatus for diagnosing defects in electrochemical gas sensors, in which the water vapor pressure of the air surrounding a sensor is suddenly changed by changing to more dry or more humid air, thereby causing a sharp change in the acidity at the working electrode, and hence, a transient current from the sensor. The response of the sensor to the change in water vapor pressure is monitored and is used for sensor diagnostics. Lack of sensitivity of the sensor to the water vapor pressure change is an indication that the sensor does not have appropriate sensitivity to the gas to be detected. The method and apparatus are particularly useful for diagnostic testing of sensors without a gas filter.

16 Claims, 3 Drawing Sheets

METHOD AND APPARATUS FOR DIAGNOSING GAS SENSORS

BACKGROUND OF THE INVENTION

1. Field of the Invention

The invention relates to testing of electrochemical sensors used for gas detection.

2. Description of Related Art

Electrochemical sensors are widely used in detecting oxygen ($O_2$) and a variety of toxic gases such as carbon monoxide (CO), hydrogen sulfide ($H_2S$), hydrogen dioxide ($SO_2$), nitrogen dioxide ($NO_2$), nitric oxide (NO), chlorine ($Cl_2$), chlorine dioxide ($ClO_2$), ozone ($O_3$), hydrogen ($H_2$) and ammonia ($NH_3$). These sensors typically comprise two or three electrodes separated by an acid or basic electrolyte, and are usually operated in amperometric mode. In operation, the working electrode potential is controlled with respect to the potential of a reference or counter electrode and the current output due to reaction of a gas at the working electrode is monitored. Electrochemical sensors need very little power to operate, are both sensitive, accurate, and can be made specific to gases of interest. However, electrochemical sensors may fail silently, i.e. without indication, for a number of reasons, including degradation of catalyst electrodes, leakage or drying out of electrolyte and broken or corroded metal pins, etc. Because electrochemical sensors are widely used in many critical applications include medical devices, safety products for protection of personnel against potentially harmful atmospheres and emission monitoring, the unrecognized failure of a sensor can have disastrous consequences. A reliable sensor diagnostic system would be a major advantage for gas detection instruments.

There are a number of patents on sensor diagnostic methods. Generally speaking, the methods fall into two major categories, electronic methods and gas test methods.

Electronic methods are disclosed, for example, in U.S. Pat. Nos. 5,202,637, 5,558,752 and 6,251,243, in which a pulse or alternating voltage of small amplitude is applied between the working electrode and the reference electrode. If the resulting current flowing through the sensor is greater than a predetermined threshold value, then the sensor is considered to be functioning correctly. Other electronic tests include those disclosed in U.S. Pat. No. 6,088,608, which describes electronic circuitry for automatically performing an integrity test based on impedance measurements, U.S. Pat. No. 6,200,443, which describes a sensor diagnostic method based on measuring capacitance by applying a small voltage, e.g. 10 mV of 10 second duration, across a sensor and measuring the rate of change of current output when the voltage is removed, and U.S. Pat. No. 6,049,283 which describes a method of detecting a fault condition by monitoring noise level from sensor output. Low noise is an indication that the sensor may have a broken wire or contact or the electrolyte may have dried out.

Gas test methods are disclosed, for example, in U.S. Pat. Nos. 5,668,302 and 6,200,443 and Japanese Publication No. 11-083792, in which a gas sensor assembly includes a gas generator which supplies a test gas, usually hydrogen, directly to the sensor on a regular basis to cause a response in the sensor. The instrument monitors the sensor's response to this test gas to determine if the sensor works properly.

Electronic methods have been widely used in gas detection instruments. A major advantage of these methods is that they can be performed automatically in an instrument on a scheduled basis. The impedance properties of electrochemical sensors can be modeled by networks of resistors and capacitors. Electronic diagnostic methods can not only check the integrity of the sensor and associated sensor control circuitry, but also determine if there is a significant reduction in the capacitance of the electrode/electrolyte interfaces, and/or a decrease in the conductivity of electrolyte. Both of these changes can reflect low gas sensitivity due to greatly reduced catalytic activity of electrodes, or insufficient electrolyte in the sensor cell.

However, electronic tests as described above can not detect if there is a leakage of electrolyte, and/or if the gas access hole is blocked. While a very low capacitance is often indicative of a low sensitivity, a large capacitance does not necessarily mean high sensor sensitivity. For example, most electrochemical sensors employing an acid electrolyte tend to have electrolyte leakage after having been exposed to high humidity for an extended period of time. Prior to electrolyte leakage occurring, the hygroscopic electrolyte absorbs a substantial amount of water from the surrounding atmosphere, resulting in an increase in electrolyte volume and eventually a high-pressure buildup inside the sensor. The high pressure forces some of the electrolyte into the working electrode beyond the amount normally present. The overall capacitance of the working electrode increases, but the sensor sensitivity becomes very low because most of the active catalyst sites in the electrode are flooded and gas diffusion into these sites becomes more difficult.

Gas test methods appears to be more reliable than electronic methods. By using a real gas, usually hydrogen ($H_2$), in the test, the method is capable of determining if the sensor is sensitive enough to a gas, and if the gas generator is located outside the sensor, this method can detect if sensor sampling hole is plugged. However, the gas concentration is difficult to control due to varying environmental conditions. Moreover, the gas generator is an electrolytic cell itself and may fail well before the sensor, since it relies on electrolysis of water to generate hydrogen gas. This method is only applicable to hydrogen and CO sensors; $O_2$ sensors and most toxic gas sensors do not respond to $H_2$ at all.

SUMMARY OF THE INVENTION

It is therefore the object of the invention to provide a simple and reliable method for diagnosing the condition of a gas sensor.

It is another object of the invention to enable detection of common sensor fault conditions, such as short circuits, broken electrical contacts, insufficient electrolyte, corroded metal pins and insufficient gas access.

It is a further object of the invention to detect if a sensor has sufficient sensitivity to detect an intended gas.

To achieve these and other objects, the invention is directed to a method for determining sensitivity of an electrochemical gas sensor including at least a working electrode and a reference electrode, and a diffusion limited inlet, comprising the steps of:

connecting the sensor to potentiostat means and means for determining output current;

establishing a base output current;

causing a sudden change in water vapor pressure at the inlet, maintaining said changed water vapor pressure over a period of at least several seconds, and recording a resultant change in output current; and comparing the change in output current to a standard to determine sensor sensitivity.

Almost all electrochemical gas sensors are operated in such a way that the working electrode potential is held sufficiently positive to oxidize an analyte gas, or sufficiently negative to reduce the gas. In the presence of a reactive gas, the current output of a sensor depends on the flux of gas through the gas diffusion path, and the number of active catalyst sites available for electrochemical reaction on the working electrode. Gas access holes, dust membranes, gas filters, and the backing support of the working electrode are all common gas diffusion barriers in electrochemical sensors. Assuming the sensor responds to the presence of a second gas, either directly or indirectly, then the second gas can be used as a reference to test the functional status of the sensor. Generally speaking, the higher the sensor's sensitivity to the second gas, the higher the sensor's sensitivity to the target gas.

Most currently used electrochemical gas sensors employ an aqueous electrolyte such as diluted sulfuric acid ($H_2SO_4$), and a working electrode made of a precious metal catalyst such as platinum (Pt). The potential of the working electrode is governed by the redox couple of oxygen ($O_2$) and water ($H_2O$) in clean air. When an equilibrium is established between oxidation of water and reduction of oxygen, the working electrode becomes stable in potential. However, if there is a sudden change in the atmosphere that affects the electrochemical reactions, the equilibrium will be broken and the potential of the working electrode will change, causing a potential difference between the working electrode and the reference electrode; as a result, current flows through the sensor.

According to the invention, a sharp change in water vapor pressure, or more generally, relative humidity at a given temperature, is made at the inlet to an electrochemical gas sensor. Because of its hygroscopic properties, the electrolyte absorbs or loses water, which causes a sharp change in the acidity at the working electrode, and hence, a current response from the sensor. Because the change in water vapor pressure takes place outside the sensor housing, the sensor's response to this vapor pressure change is very similar to its response to the entry of a reactive gas to the sensor. If the response to the pressure change is too small or there is no response at all, the sensor will not be sensitive enough to detect any other reactive gas.

The change in water vapor pressure, or relative humidity, necessary to cause a measurable sensor response is thought to be about 5%. The larger the change, the greater the response of the sensor. The source of the change in water vapor pressure may, in fact, be air in either damp or dry areas, ambient air that has passed through a desiccator or a humidifier, or a tank of compressed air, which is sometimes called "dry air" and is extremely low in water content. The air which is tested as a result, however, will be air of "ambient" composition except for a change in water vapor pressure.

The change in water vapor pressure at the inlet to the sensor must be conducted in a reproducible manner, with a properly functioning sensor then delivering a reproducible change in output current. The normal change in output current will depend on the sensor itself, and will be determined from test results from a large number of sensors of a particular type, and the desired sensor sensitivity. Advantageously, a normal value, e.g. −50 nA, will be stored in the instrument as a threshold value for comparison with the test value. If the test value is insufficient, the instrument can be taken out of service and examined for defects. Alternatively, the sensor response can be compared with a previous response in the same test, and the sensor will be considered to be failing if there is a significant decrease in the output value.

The invention is also directed to an apparatus for carrying out the method, including a diffusion limited electrochemical gas sensor cell, means for causing a sudden change in water vapor pressure at the inlet of the cell, and means for connecting the cell inlet with the vapor pressure changing means. Preferably, the apparatus will also include control means, including potentiostat means for operating the cell, means for determining and/or recording cell output current, means for controlling the duration of the change in water vapor pressure, and means for comparing the change in output current with a normal value. Some of the control and/or recording means may be at a remote location, with control by telephone, wireless communication or computer network.

DESCRIPTION OF THE PREFERRED EMBODIMENTS

Figure 1:
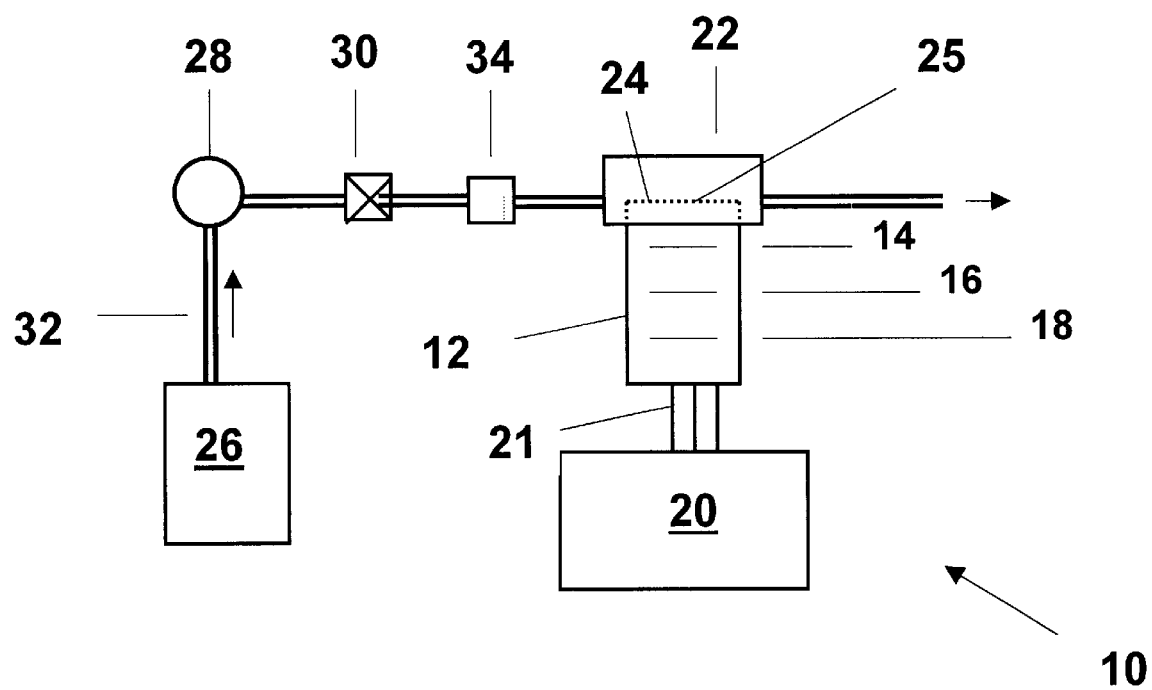
FIG. 1 is a schematic diagram of an apparatus for performing the method of the invention.

According to the invention, a sensor's response to a target gas is mimicked by changing the water vapor pressure, or humidity of the air the sensor is sampling, and measuring the sensor's response to the change.

Most electrochemical gas sensors have two or three electrodes and a water-based electrolyte, with a platinum/air (or other precious metal/air) electrode being used as a reference electrode. The potential of a platinum/air electrode in an acid electrolyte is governed by the following redox reaction:

$$O_2 + 4H^+ + 4e^- \leftrightharpoons H_2O \qquad (1)$$

According to the Nernst equation, the equilibrium potential of the platinum/air electrode at room temperature under 1 atmosphere can be expressed as:

$$E = E_{O_2/H_2O}^{O'} + 0.059 \log[H^+] + 0.015 \log(pO_2) \qquad (2)$$

where $E_{O_2/H_2O}^{O'}$ is the formal potential of oxygen electrode, $[H^+]$ is the concentration of hydrogen ions, and $pO_2$ is the partial pressure of oxygen gas. Equation 2 shows that the electrode potential is dependent on the oxygen pressure, and the concentration of hydrogen ions.

The working electrode may be made a precious metal catalyst such as Pt, gold (Au), silver (Ag), iridium (Ir), ruthenium (Ru), palladium (Pd), rhodium (Rh) or an alloy of precious metals depending on the type of gas the sensor is intended to detect. When exposed to clean air, the working electrode potential is controlled by the $O_2$ reduction and $H_2O$ oxidation regardless of catalyst materials. According to equation 2, if the oxygen pressure and acidity are the same at both the working electrode and at the reference electrode, the two electrodes will have equal potentials, and there will be no current flowing through the electrodes if they are connected electrically without applying a bias voltage. Many toxic gas sensors including CO and $H_2S$ sensors work on this principle. If, however, the working electrode is made more negative with respect to a stable reference electrode potential through a potentiostat, as is the case of a regular oxygen sensor, a new electrochemical equilibrium favoring oxygen reduction will be established at the working electrode.

The electrolyte is usually chosen from acid electrolytes such as dilute $H_2SO_4$ and phosphoric acid ($H_3PO_4$), and basic electrolytes such as potassium acetate. Because of its hygroscopic properties, the electrolyte absorbs water vapor under conditions of high water vapor pressure, and allows water to evaporate at very low ambient water vapor pressure. The rate of water exchange between the electrolyte and ambient air depends on concentration of the electrolyte, water vapor pressure, and dimensions of the gas path into the sensor. When the rate of water evaporation equals the rate of water absorption, the concentration of electrolyte becomes stable in the air. The same water vapor pressure always balances a given acid concentration, fairly independently of temperature.

The water exchange between electrolyte and surrounding atmosphere may not reach equilibrium even after several weeks. The equilibrium between $H_2O$ oxidation and $O_2$ reduction, on the other hand, can be obtained within a very short period of time. A toxic gas sensor therefore shows a base current close to zero under normal operating conditions. Assuming there is a rapid, large increase in water vapor pressure at the gas inlet to the sensor, such that the changed water vapor pressure is much higher than the pressure needed to balance the concentration, the electrolyte will quickly absorb water vapor. As a consequence, $H^+$ ions are diluted at the working electrode, which is in direct contact with air. According to equation 2, the potential of the working electrode will tend to decrease as $[H^+]$ decreases. Because the working electrode potential is controlled by an external potentiostat with respect to the reference electrode potential, water starts to be oxidized at the working electrode and a positive current is delivered. A maximum current is obtained when $[H^+]$ reaches a lowest value.

As $H_2O$ is oxidized to $O_2$ at the working electrode, more $H^+$ ions are generated at the working electrode to offset the decrease due to dilution by absorbed water, and at the same time, an opposite reaction, i.e. the reduction of $O_2$ to $H_2O$, proceeds at the counter electrode, or the counter/reference electrode if this is a two electrode cell. The counter electrode reaction consumes $H^+$ ions, causing a decrease in $[H^+]$ at the reference electrode. The amplitude of current gradually decreases as $H^+$ ions at both the working electrode and the reference electrode change to the same concentration.

Likewise, when there is a rapid, large decrease in water vapor pressure at the gas inlet to the sensor, water quickly evaporates from the electrolyte, causing a sharp increase in the concentration of $H^+$ ions, and a tendency for the potential of the working electrode to increase. $O_2$ begins to be reduced at the working electrode and a negative is delivered. The current reaches a maximum value when $[H^+]$ is the highest, and then decreases as the difference between $H^+$ concentrations at the working and reference electrodes decreases.

Although most electrochemical gas sensors have a working electrode made of precious metals, to which the above rules apply, there are a few sensors using a carbon working electrode. For example, gas sensors type 7NDH and type 3CLH manufactured by City Technology Limited (UK), for the detection of $NO_2$ and $Cl_2$ have a working electrode and a reference electrode fabricated from carbon, and a counter electrode comprising a Pt catalyst. Carbon is a very poor catalyst for $O_2$ reduction and $H_2O$ oxidation. The equilibrium potentials in acid electrolyte of carbon electrodes are found to be about 170–200 mV more negative than those of precious metals, possibly because of chemisorbed species such as O, H, —OH and/or functional groups of organic substances that control the redox potential. When the electrolyte absorbs water at high water vapor pressures, $[H^+]$ is momentarily higher at the working electrode than at the carbon reference electrode. As a consequence, an electrochemical reaction takes place at the working electrode to minimize this $[H^+]$ change and a negative current transient is obtained. When the water vapor pressure suddenly decreases, electrochemical oxidation proceeds at the working electrode, and a positive current response is obtained. This type of sensor thus has exactly opposite response to water vapor pressure change compared with most others having a working electrode made of precious metal catalysts.

Water vapor pressure can be described conveniently by humidity. Relative humidity is the ratio, expressed in percent, of the actual water vapor pressure to the saturation water vapor pressure, which is a unique function of temperature. Most electrochemical sensors can work continuously within 15% to 90% relative humidity; long term exposure to extremely high or low humidity will cause electrolyte leakage or drying-out, respectively. Normal indoor air has about 35–70% relative humidity, but this is very dependent on temperature and weather conditions.

The greater the difference in water vapor pressure, the greater the amplitude of the transient response. The minimum change in water vapor pressure, or relative humidity to cause a measurable sensor change is generally greater than 5%, but is dependent on the type of sensor. For example, a sensor with more restrictive gas diffusion path gives a small response to the same water vapor change, which agrees with its small sensitivity to a reactive gas.

Water vapor pressure can be changed in many ways, including adding water to, or removing water from existing air, changing the air the sensor is sampling, moving the sensor into air of different humidity level, or delivering dry or humid air to the sensor head by forced convection means.

According to the invention, the change in water vapor pressure should be completed as quickly as possible, preferably within two seconds. A slow change will not cause a large current response from the sensor. The new water vapor pressure which is established should be maintained for a period of about 5–120 seconds, and preferably 15–60 seconds. Among various water vapor pressure change means, forced convection is very easy to implement, not requiring any special equipment. Upon applying a directed flow of air from another source, air at the sensor inlet is replaced by new air, and the water vapor pressure is rapidly changed.

In laboratory testing, it was found that the air flow should be at least 100 ml/min and the flow rate is preferably between 100–500 ml/min; however the minimum and optimum flow ranges will depend greatly on the physical apparatus and experimental setup. In this respect, a directed flow through a fine tube directly at the working electrode surface could well achieve a measurable response with less than 100 ml/min. Further increasing flow rate does not increase sensor response.

FIG. 1 schematically shows an apparatus 10 which can be used to perform the method of the invention. An electrochemical sensor 12 with three electrodes, a working electrode 14, a reference electrode 16 and a counter electrode 18, is connected to an instrument 20 through electrode leads 21. The sensor 12 is installed in a gas flow system through sensor adaptor 22, with sensor head 24 having gas access holes 25 placed in the gas flow path. The gas delivery system includes a dry air source 26 which in this embodiment is a compressed clean air cylinder with regulator, a flow meter 28 controlling the air flow rate, a solenoid activated switching valve 30 which admits air from the cylinder and Teflon tubing 32 of approximately 2.0 mm inner diameter connecting the elements of the gas delivery system. A gas washing device 34 is added to the gas delivery system only when high water vapor pressure is needed.

In order to perform a diagnostic test, the gas switching all a valve 30 is first in the OFF position, and the sensor 12 is exposed to clean, quiescent ambient air of relative humidity around 40–65%. The instrument 20 is then set to diagnostic mode in which current response is monitored. The gas valve 30 is turned on and air starts to flow over the sensor head 24. After about one minute the air is turned off. The diagnostic software in the instrument 20 examines the sensor response to see if the sensor sensitivity is sufficient. Low sensitivity indicates the sensor does not function properly.

Instrument 20 may also include means for connection to a remote monitor, for example, over a telephone line or a computer network. While the potentiostat will be located in the immediate vicinity of the cell, the other control and recording functions may be at a remote location.

Figure 2:
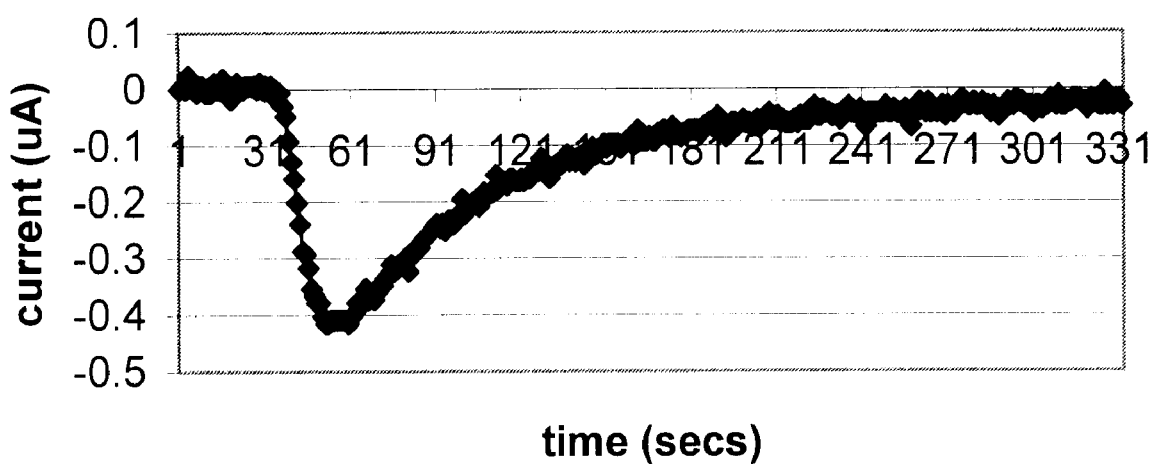
FIG. 2 is a graph of the response of a three-electrode $H_2S$ gas sensor to dry air vs. time, with air flow at 200 ml/min.

FIG. 2 shows a typical response of a properly functioning $H_2S$ sensor, connected in a system such as is shown in FIG. 1, to dry air. The sensor has three electrodes, a 420 nA/ppm sensitivity to $H_2S$ gas, and was connected to a potentiostat with zero bias voltage. After the sensor had stabilized in clean ambient air at about 55% relative humidity, compressed air starts to flow at 200 ml/min over the top of the sensor. As shown in FIG. 2, the sensor shows a transient response to the airflow. The response reaches a maximum amplitude of current within 10–15 seconds, and then decays. The current slowly returns to its original value in about 5 minutes when the dry air continues flowing at a stable flow rate, showing that the sensor is regaining a new equilibrium in the dry air.

Figure 3:
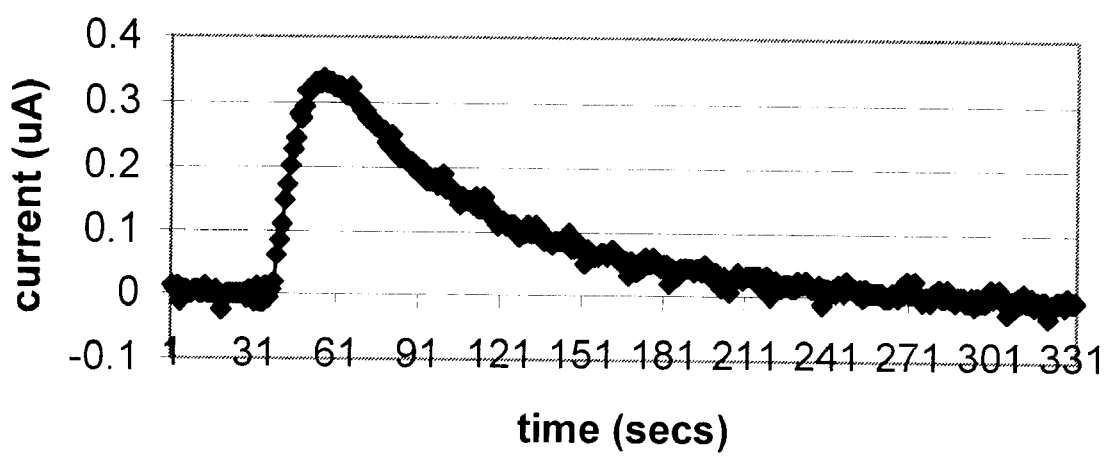
FIG. 3 is a graph of the response of the sensor of FIG. 2 to humid air at the same flow rate.

FIG. 3 shows the response of the same sensor to humid air which has a relative humidity about 95%. Unlike its response to dry air, the sensor gives a positive current response. The current reaches a maximum value in about 15 seconds, and then gradually decays.

All electrochemical gas sensors have gas access holes to allow gas to reach the working electrode, whereupon the reactive gas is either reduced or oxidized or participates in or otherwise affects a redox reaction. Almost all electrochemical gas sensors are diffusion limited, i.e. the output of the sensor is controlled by the rate of diffusion through a diffusion barrier. Since the method of the invention measures the sensor's response to a change in water vapor pressure outside the sensor cell, a change in the sensor's sensitivity to the gas due to change in the gas diffusion path will be reflected by a change in sensor's response to the water vapor pressure change. The more restrictive the gas diffusion barrier, the smaller the sensor's sensitivity to a reactive gas and the smaller sensor's response to the air pressure change. Therefore, a diagnostic method based on the invention can detect if the gas access hole is partly or completely blocked.

The method is particularly useful for oxygen sensors that have deep and tiny gas access holes to restrict oxygen diffusion into the sensor. The capillary holes in the diffusion barriers of oxygen sensors are typically 0.1–0.4 mm in diameter, and 1–3 mm deep. These holes are easily clogged when sensors are installed in demanding environmental areas such as oil fields, chemical plants and damp areas.

The same principle applies to other gas barriers such as dust membranes, porous backing layers of working electrodes and gas filters, if any. These gas diffusion barriers may deteriorate or become partly blocked due to dust, oil deposit, water condensation or electrolyte leakage from the cell. However, some gas filters such as activated carbon may absorb water vapor when water vapor pressure suddenly increases, causing a small sensor response possibly too small to measure. In this case, dry air instead of humid air should be used. The choice of dry or humid air will depend on the nature of the gas filter.

Likewise, the sensitivity of an electrochemical sensor may decrease due to degraded catalyst electrodes. A fresh sensor usually has the highest catalyst activity, but the activity decreases over time due to decreased number of active catalyst sites available for electrochemical oxidation or reduction of a reactive gas. For example, almost every sensor has reduced sensitivity after having been exposed to low humidity air for an extended period of time because the working electrode loses part of its electrical contact with electrolyte. When tested with high water vapor pressure, only the active catalyst sites that are in contact with electrolyte are available for electrochemical oxidation of water, or reduction of oxygen. Therefore, the response of the sensor to the change in water vapor pressure should be lower than before.

Although the majority of electrochemical gas sensors use a platinum/air (or other metal or carbon/air) reference electrode, a few sensors such as two electrode oxygen sensors, and ammonia sensors described in U.S. Pat. Nos. 5,234,567 and 6,248,224 have a reference electrode made of lead, silver, zinc, etc. The ammonia sensors use an indirect method in which ammonia is dissolved in an aqueous electrolyte to cause a pH change so that a chemical substance in the electrolyte is converted through a chemical reaction to an active species that can be oxidized at the working electrode. The method of the invention can be applied to these sensors as well, since a sharp change in water vapor pressure causes a pH change at the working electrode, which perturbs the electrochemical equilibrium potential at the working electrode. The potentiostat then causes a current transient to flow through the cell to minimize this perturbation.

A diagnostic method based on the invention is suitable for checking the functional status of a sensor and instrument in service, since the test can be conducted without the need to open the instrument to test the sensor. For example, $O_2$ and toxic gases such as CO and $H_2S$ in confined spaces or remote locations are usually detected using the sample draw method by combining a sample draw system with a gas detection instrument. The sample draw system typically comprises a motorized pump, an adaptor cap which enables the instrument to work with the system, and a length of tubing. When fit into the adaptor cap, sensors in the instrument are exposed to air confined in a small gas compartment. The motorized pump draws sample air to this compartment at a fixed flow rate of typically around 300–700 ml/minutes for the instrument to detect. A diagnostic test can be performed in clean air prior to each use. The humid air can be created easily, for example, by partially filling a narrow mouthed clear bottle of about 500 ml capacity with clean running water, and then shaking hard and emptying the bottle. The relative humidity in the bottle should be higher than 90%. According to the invention, the gas detection instrument is first turned on in clean ambient air, and after a couple of minutes during which the instrument stabilizes, the instrument automatically enters, or is manually set to, diagnostic mode. The sampling tube is placed into the wet bottle with its open end close to the bottom of the bottle. The motorized pump is then turned on and humid air starts to flow through the tubing and the sample gas compartment; after about 30 seconds to 1 minute the pump stops running. The diagnostic software in the instrument examines sensor outputs before and after the air flow to see if the sensitivity exceeds a pre-set threshold value. Low sensitivity indicates the sensor has low sensitivity to the gas to be detected.

In addition to drawing humid or dry air to the sensor, a device incorporating a drying agent, such as a Fisher Scientific humidity sponge, Drierite drying tube, Scienceware desiccant cartridges, or a device that increases humidity such as a water bubbler or gas washing bottle, can be placed before of after the motorized pump in the gas delivery system. Depending on the application, other apparatus will be readily apparent to those skilled in the art given the benefit of this disclosure.

A method based on the invention can easily be used to conduct bump tests on other instruments, as well. Some detectors are installed in inaccessible locations, such as on chimneys or construction towers making it difficult to conduct routine sensor sensitivity test. A diagnostic system based on the invention may be incorporated with the instrument that would allow periodic and automatic testing of the sensor between the regular calibration intervals.

During the entire diagnostic test, a sensor is only minimally perturbed. The transient response to water pressure change is usually at sub-ppm level for most toxic gases, and a fraction of 1% for oxygen sensors. Thus, at the conclusion of the test, the sensor is immediately available for use again. The method of the invention is advantageous over other in-situ diagnostic methods in that: (1) no toxic gases are required; (2) low sensitivity of the sensor can be detected; 3) a blocked gas inlet can be detected; 4) the method has a low cost and is easy to implement, and 5) the method is applicable to almost all electrochemical gas sensors using an aqueous electrolyte, in particular to those without a gas filter.

EXAMPLE 1

Four old, lab-built three-electrode hydrogen sulfide ($H_2S$) sensors having normal capacitance and conductivity were connected to in-house potentiostats. The response from the sensors was measured as the sensors were exposed to air from a cylinder of compressed air at an air flow of 200 ml/min. These sensors gave a negative current in response to the dry air, which reached a maximum amplitude in about 10–15 seconds, and then started to decay. The amplitude of each current response varied from sensor to sensor. The sensors were tested with 20 ppm $H_2S$ in air, and showed different sensitivities. As shown in Table 1 below, the peak currents of sensor response to air flow and sensitivity to $H_2S$ gas show a good correlation. Higher amplitude of the sensor response to dry air corresponds to higher sensor sensitivity. Sensor No. 1 has essentially no response to dry air and its sensitivity to $H_2S$ gas is almost negligible.

TABLE 1

Comparison of $H_2S$ sensor sensitivity to $H_2S$ gas and responses to dry air at 200 ml/min

| Sensor No. | 1 | 2 | 3 | 4 |
|---|---|---|---|---|
| Response to air flow (nA) | −3 | −180 | −30 | −210 |
| $H_2S$ sensitivity (nA/ppm) | 1 | 309 | 50 | 360 |

EXAMPLE 2

Three nitrogen dioxide sensors type 7NDH made by City Technology Ltd, UK were each connected to a potentiostat with a zero bias voltage. After their base current stabilized in clean ambient air, compressed air which has gone through a gas wash device started to flow at 200 mL/min at the gas inlet. The response was approximately −155 nA, −195 nA, −137 nA, respectively for the three sensors to the humid air, while their sensitivities to $NO_2$ gas were −804 nA/ppm, −875 nA/ppm, and −698 nA/ppm, respectively.

EXAMPLE 3

Four ammonia ($NH_3$) sensors type A7AM made by City Technology Ltd (UK) were each connected to a potentiostat with a bias voltage +300 mV between working electrode and reference electrode. When stabilized, air from a compressed air cylinder starts to flow over the top of each sensor at 300 ml/min. All the sensors show a transient response to the dry air. The peak currents were −30 nA, −25 nA, −28 nA and −35 nA, respectively. When tested with $NH_3$ gas their sensitivities were all within 55±15 nA/ppm as specified.

EXAMPLE 4

Four two-electrode oxygen sensors including two type 4C made by City Technology Ltd and two type Oxygen SL made by Sixth Sense, both UK manufacturers, were each connected to a potentiostat. For each sensor, the working electrode was connected to the working electrode lead, and the counter electrode connected to pre-shorted counter and reference electrode leads of the potentiostat. In clean air, the sensors gave steady state current outputs of −215 $\mu A$, −210 $\mu A$, −412 $\mu A$ and −385 $\mu A$, respectively. When dry air started to flow at an air flow of 500 ml/min, the current outputs changed by approximately −5 $\mu A$ and −6 $\mu A$ for the type 4C, and by −12 $\mu A$ and −10 $\mu A$ for the type Oxygen SL.

What is claimed is:

1. A method for determining loss of sensitivity of an electrochemical gas sensor including at least a working electrode and a reference electrode, an aqueous electrolyte and a diffusion limited inlet, comprising the steps of:
   connecting the sensor to potentiostat means and means for determining output current;
   establishing a base output current;
   causing a sudden change in water vapor pressure at the inlet, maintaining said changed water vapor pressure over a period of at least a few seconds, and recording a resultant change in output current; and
   comparing the change in output current to a standard to determine sensor sensitivity.

2. A method according to claim 1, wherein the change in water vapor pressure is caused by exposing the sensor to air of either low or high relative humidity.

3. A method according to claim 1, wherein the change in water vapor pressure is caused by adding, or removing water vapor from the air surrounding the sensor.

4. A method according to claim 1, wherein the change in water vapor pressure is caused by directing a stream of dry or human air at the inlet.

5. A method according to claim 4, wherein dry or humid air has a flow rate of about 100–500 ml/min.

6. A method according to claim 1, wherein the sudden change in water vapor pressure is a change of over 5%.

7. A method according to claim 1, wherein said changed water vapor pressure is maintained for a period of about 5–120 seconds.

8. A method according to claim 1, wherein said changed water vapor pressure is maintained for a period of about 15–60 seconds.

9. A method according to claim 1, wherein the electrolyte is an aqueous acid or basic electrolyte, and the working electrode comprises at least one element selected from the group consisting of platinum, gold, iridium, ruthenium, silver, palladium, rhodium and electrically conductive carbon.

10. An apparatus including an electrochemical gas sensor cell and a means for self-diagnosing a loss of sensitivity of the cell, comprising:

an electrochemical gas sensor cell including at least a working electrode and a reference electrode, an aqueous electrolyte and a diffusion limited inlet;

means for causing a sudden change in water vapor pressure and maintaining a changed water vapor pressure at said inlet; and means for connecting said means for causing with said inlet.

11. An apparatus according to claim 10, further comprising instrument means connected to said sensor cell, including control means for said gas sensor cell and means for determining output current of said cell.

12. An apparatus according to claim 11, wherein said control means comprises means for storing an operative value for said sensor cell, and means for comparing output current to said value.

13. An apparatus according to claim 11, wherein at least one element of said instrument means is a location remote from said cell, and connected by a telephone line or a computer network or wireless communications means.

14. An apparatus according to claim 10, wherein said control means includes means for causing a water vapor pressure change of predetermined duration.

15. An apparatus according to claim 10, wherein said means for causing comprises a tank of compressed air, a container containing humid air, a gas drying or wetting agent or device, or a pump.

16. An apparatus according to claim 10, wherein said means for connecting comprises a cover for said inlet and tubing for connecting said cover to said means for causing.

* * * * *